United States Patent
Han et al.

(10) Patent No.: US 9,766,209 B2
(45) Date of Patent: Sep. 19, 2017

(54) APPARATUS FOR DETECTING PIPE WALL THINNING AND METHOD THEREOF

(71) Applicant: Korea Atomic Energy Research Institute, Daejeon (KR)

(72) Inventors: Soon-Woo Han, Hwaseong-si (KR); Doo-Byung Yoon, Daejeon (KR); Jin-Ho Park, Daejeon (KR); Hong Pyo Kim, Daejeon (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 218 days.

(21) Appl. No.: 14/522,359

(22) Filed: Oct. 23, 2014

(65) Prior Publication Data

US 2015/0185186 A1    Jul. 2, 2015

(30) Foreign Application Priority Data

Dec. 31, 2013    (KR) .................. 10-2013-0168727

(51) Int. Cl.
*G01N 29/12* (2006.01)
*G01N 29/04* (2006.01)
*G01H 13/00* (2006.01)

(52) U.S. Cl.
CPC ........... *G01N 29/045* (2013.01); *G01H 13/00* (2013.01); *G01N 29/12* (2013.01); *G01N 2291/014* (2013.01); *G01N 2291/2634* (2013.01)

(58) Field of Classification Search
CPC .......... G01H 1/00; G01H 13/00; G01N 29/12; G01N 29/11; G01N 29/14; G01N 29/045;

(Continued)

(56) References Cited

U.S. PATENT DOCUMENTS 3,916,699 A * 11/1975 Moran ................... G01N 29/14
                                                              73/592
4,912,683 A *  3/1990 Katahara ............... E21B 47/082
                                                              181/105

(Continued)

FOREIGN PATENT DOCUMENTS

JP    6-201364 A    7/1994
JP    7-086450 B2   9/1995

(Continued)

OTHER PUBLICATIONS

Han, Soo-Woo et al., "Monitoring of wall thinning of a pipe by measuring natural frequencies of shell vibration modes", The Korean Society for Noise and Vibration Engineering (KSNVE), 2013 Autumn Conference Proceedings, 8 pages.

*Primary Examiner* — Laura Martin
*Assistant Examiner* — Rose M Miller
(74) *Attorney, Agent, or Firm* — Knobbe Martens Olson & Bear LLP

(57) ABSTRACT

Disclosed are an apparatus for detecting pipe wall thinning, which measures a natural frequency of a pipe and determines a level of the pipe wall thinning, and a method thereof.

The apparatus for detecting the pipe wall thinning includes a hitting member 10 for hitting the pipe T, a vibration measurement sensor 20 which measures a vibration signal generated when the pipe T is hit with the hitting member 10, and a control part 30 which compares the natural frequency calculated from the vibration signal measured from the vibration measurement sensor 20 with a natural frequency generated from a normal pipe in which wall thinning does not occur, and determines the level of the wall thinning of the pipe T.

6 Claims, 14 Drawing Sheets

(58) Field of Classification Search
CPC ............... G01N 29/42; G01N 29/4436; G01N 2291/2634; G01N 2291/0258; G01N 2291/014; G01N 2291/0289; G01M 3/243; G01M 7/00; G01M 7/08
USPC ...... 73/579, 582, 586, 587, 588, 592, 12.01, 73/622, 623
See application file for complete search history.

(56) References Cited

U.S. PATENT DOCUMENTS

| | | | |
|---|---|---|---|
| 5,756,898 A * | 5/1998 | Diatschenko | G01B 17/02 73/40.5 A |
| 2005/0011278 A1* | 1/2005 | Brown | G01F 1/666 73/861.18 |
| 2010/0324839 A1* | 12/2010 | Martin | G01M 3/243 702/56 |
| 2011/0154902 A1* | 6/2011 | Fisk | G01N 29/265 73/592 |

FOREIGN PATENT DOCUMENTS

| | | |
|---|---|---|
| JP | 2004-325224 A | 11/2004 |
| JP | 2012107918 A | 6/2012 |

* cited by examiner

FIG. 3A

| DEGREE | 2 | 3 | 4 |
|---|---|---|---|
| T | 3215 | 8666 | 15651 |
| T1 | 2823 / 3193 | 7873 / 8483 | 13952 / 15126 |
| T2 | 2807 / 3118 | 7888 / 8142 | 13942 / 14517 |
| T3 | 2821 / 2950 | 7714 / 7875 | 13938 / 14163 |
| T4 | 2651 / 2795 | 7355 / 7423 | 13445 / 13539 |

FIG. 5A

| DEGREE | 2 | 3 | 4 |
|---|---|---|---|
| T | 3215 | 8666 | 15651 |
| T5 | 3054 / 3136 | 8346 / 8375 | 15101 / 15106 |
| T6 | 2943 / 3180 | 8139 / 8435 | 14564 / 15077 |
| T7 | 2823 / 3193 | 7873 / 8483 | 13952 / 15126 |

FIG. 6A

| DEGREE | 2 | 3 |
|---|---|---|
| T | 3169 | 8588 |
| T1 | 2806 / 3150 | 7837 / 8431 |
| T2 | 2753 / 3062 | 7793 / 8031 |
| T3 | 2750 / 2887 | 7581 / 7737 |
| T4 | 2631 / 2769 | 7306 / 7401 | i = 0 i = 1 i = 2

APPARATUS FOR DETECTING PIPE WALL THINNING AND METHOD THEREOF

CROSS-REFERENCE TO RELATED APPLICATION

This application claims priority to and the benefit of Korean Patent Application No. 10-2013-0168727, filed on Dec. 31, 2013, the disclosure of which is incorporated herein by reference in its entirety.

BACKGROUND

1. Field of the Invention

The present invention relates to an apparatus for detecting pipe wall thinning and a method thereof, and more particularly, to an apparatus for detecting pipe wall thinning, which is capable of detecting and analyzing a change in a natural frequency of a pipe and thus inspecting the wall thinning of the pipe, and a method thereof.

2. Discussion of Related Art

In facilities, cases in which wall thinning and fracture of pipes occur according to deterioration of the pipes installed in the initial construction have been reported. In particular, since the Mihama nuclear power plant accident due to the wall thinning and fracture of pipes, an interest in a technique for finding pipe wall thinning has increased.

In power plants, to find pipe wall thinning, a thickness measurement technique using an ultrasonic thickness indicator is widely used on the spot. However, such a measurement technique takes a lot of time because a plurality of measuring points distributed on a pipe surface should be measured one by one. If the plurality of measuring points are not measured, the reliability of the results of a measurement is degraded.

Therefore, high attention is placed on a technique capable of maintaining the accuracy of the pipe thickness measurement and rapidly checking whether the pipe wall thinning occurs, as compared with an existing technique. Further, by primarily rapidly finding the pipe wall thinning and a level thereof, selecting a pipe in which wall thinning will be precisely monitored according to such a process, and then continuously and concentrically monitoring the selected pipe, it is possible to increase monitoring efficiency of the wall thinning and also to enhance safety of the equipment, as compared with the existing wall thinning measuring technique.

RELATED DOCUMENTS

Patent Documents (Patent document 1) Japanese Patent Publication No. 2012-107918

SUMMARY OF THE INVENTION

The present invention is directed to an apparatus for detecting pipe wall thinning, which is capable of determining whether pipe wall thinning occurs using a property in which a natural frequency of a pipe having wall thinning is lower than a natural frequency of a pipe with no wall thinning, and thus reducing a measurement time, and a method thereof.

Also, the present invention is directed to an apparatus for detecting pipe wall thinning, which is capable of determining whether pipe wall thinning occurs using a phenomenon in which the natural frequency in the same degree is branched into two when pipe wall thinning occurs, and thus reducing a measurement time and also enhancing the reliability of the determination, and a method thereof.

According to an aspect of the present invention, there is provided an apparatus for detecting wall thinning, including a vibration measurement sensor which measures a vibration signal generated from a pipe to be measured by being hit with a hitting member to calculate a natural frequency, and a control part which compares the natural frequency calculated from the vibration signal measured from the vibration measurement sensor with a natural frequency generated from a normal pipe in which wall thinning does not occur, and determines a level of the wall thinning of the pipe.

The natural frequency may be reduced when the wall thinning occurs uniformly in the pipe, and the control part may detect this to determine the level of the wall thinning of the pipe.

When the wall thinning locally occurs in the pipe, the natural frequency may be branched into two or more in the pipe of which a thickness is locally reduced, and the control part may observe the branching phenomenon of the natural frequency to determine whether there is wall thinning in the pipe and a shape thereof.

When the hitting member is a portable hammer, the control part may measure an auto power spectrum APS upon measuring the natural frequency, and may extract the natural frequency.

According to another aspect of the present invention, there is provided a method of detecting local wall thinning in a pipe for estimating whether wall thinning occurs and a shape thereof, including a measuring process of a vibration measurement sensor installed on a pipe measuring a vibration signal when a pipe to be measured is hit; a natural frequency measuring process of measuring a natural frequency of the pipe; a calculating process in which a control part calculates a ratio or a difference value between natural frequencies of the pipe, which are branched in the same degree, based on the measured natural frequency; and a determining process in which the control part determines whether there is wall thinning and a shape thereof based on a value calculated in the calculating process.

When the pipe is hit using a hitting member installed on the pipe, an impact signal measuring process in which the vibration measurement sensor measures the vibration signal of the hitting member may be performed before the natural frequency measuring process.

When the pipe is hit by a portable hammer, the natural frequency measuring process may include extracting the natural frequency from an auto power spectrum APS of a signal measured by the vibration measurement sensor.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 3A and FIG. 3B are graphs analyzing a change in a natural frequency according to a level of the wall thinning of the pipe illustrated in FIGS. 2A-2C;

FIG. 5A and FIG. 5B are graphs illustrating a change in a natural frequency ratio in the same degree according to a shape of the wall thinning of the pipe illustrated in FIGS. 4A-4C;

FIG. 6A and FIG. 6B are graphs illustrating a result of the experiment of the change in the natural frequency according to the level of the wall thinning of the pipe illustrated in FIGS. 2A-2D;

DETAILED DESCRIPTION OF MAIN ELEMENTS

| | |
|---|---|
| S1: measuring process | S2: natural frequency measuring process |
| S3: ratio calculating process | S4: determining process |
| T: pipe | 30: control part |

DETAILED DESCRIPTION OF EXEMPLARY EMBODIMENTS

Hereinafter, an apparatus for detecting pipe wall thinning and a method thereof according to one embodiment of the present invention will be described in detail below with reference to the accompanying drawings.

Figure 1:
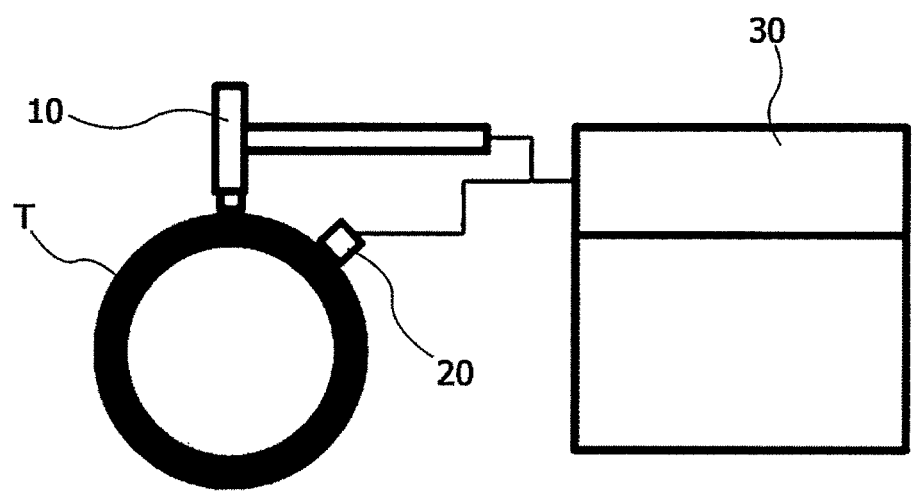
FIG. 1 is a schematic view schematically illustrating an apparatus for detecting pipe wall thinning according to a first embodiment of the present invention.
Figure 2A:
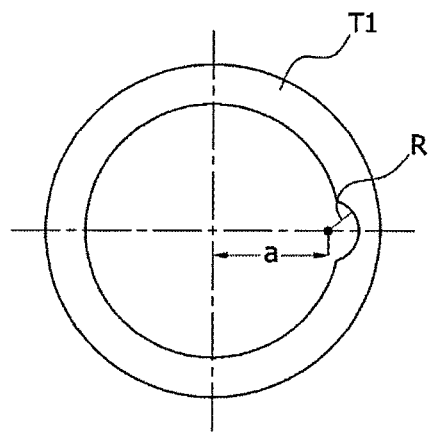
FIG. 2A, FIG. 2B, FIG. 2C and FIG. 2D are cross-sectional views of a pipe used in an experiment.
Figure 2B:
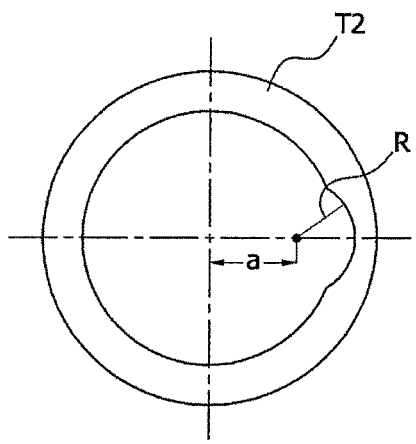
Figure 2C:
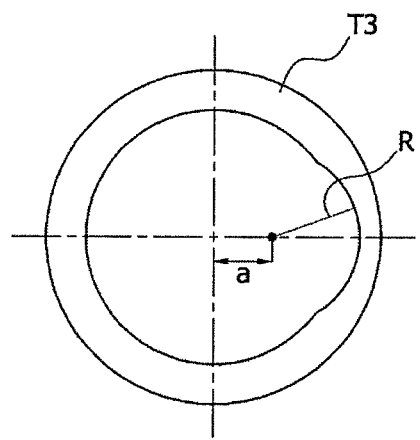
Figure 2D:
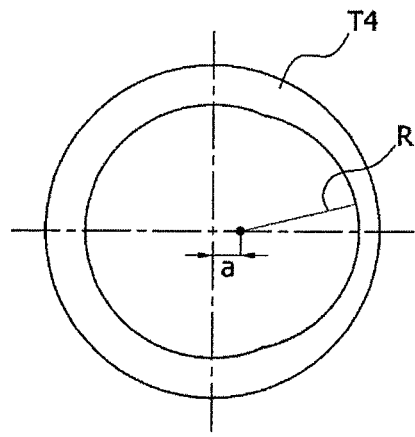
Figure 3B:
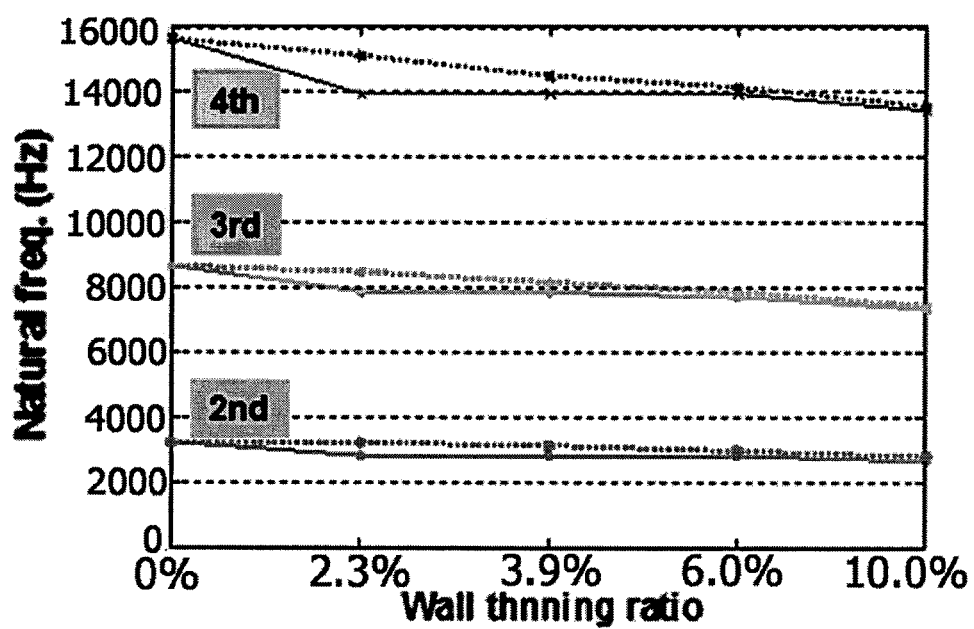
Figure 4A:
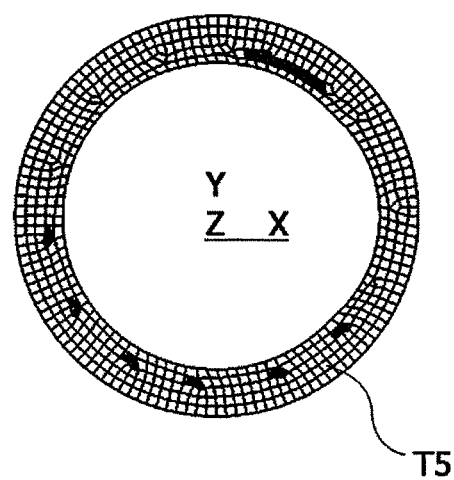
FIG. 4A, FIG. 4B and FIG. 4C are cross-sectional views of a pipe used in another experiment.
Figure 4B:
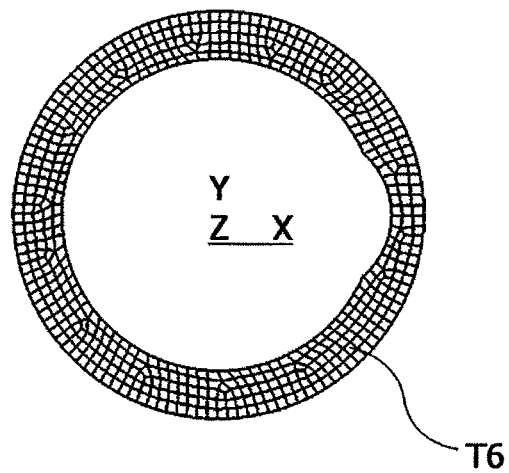
Figure 4C:
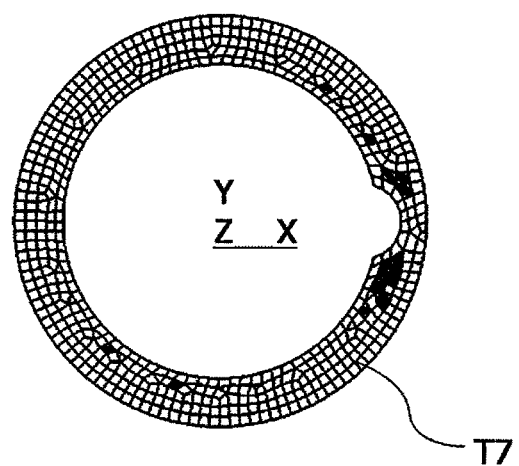
Figure 5B:
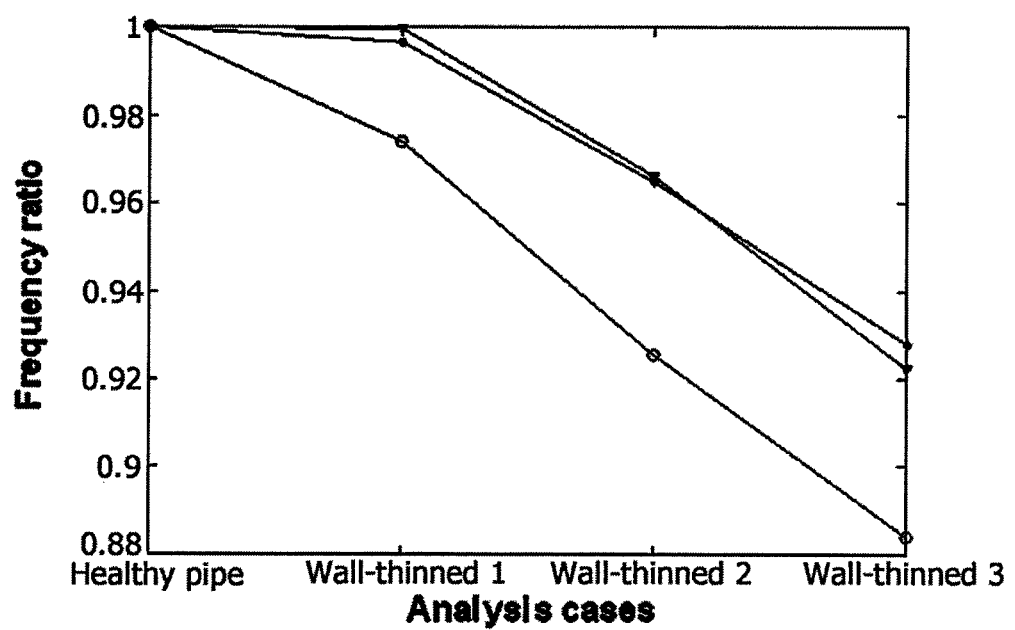

FIG. 1 is a schematic view schematically illustrating an apparatus for detecting pipe wall thinning according to a first embodiment of the present invention, FIG. 2A, FIG. 2B, FIG. 2C and FIG. 2D are cross-sectional views of a pipe used in an experiment, FIG. 3A and FIG. 3B are graphs analyzing a change in a natural frequency according to a level of the wall thinning of the pipe illustrated in FIGS. 2A-2C, FIG. 4A, FIG. 4B and FIG. 4C are cross-sectional views of a pipe used in another experiment, FIG. 5A and FIG. 5B are graphs illustrating a change in a natural frequency ratio in the same degree according to a shape of the wall thinning of the pipe illustrated in FIGS. 4A-4C, FIG. 6A and FIG. 6B are graphs illustrating a result of the experiment of the change in the natural frequency according to the level of the wall thinning of the pipe illustrated in FIGS. 2A-2D, and FIG. 7 is a flowchart illustrating a method of detecting the local wall thinning in the pipe according to the first embodiment of the present invention.

As illustrated in FIGS. 1 to 6, an apparatus for detecting pipe wall thinning according to one embodiment of the present invention includes a hitting member 10 with which a pipe T to be measured is hit, a vibration measurement sensor 20 which is installed on the pipe T to be spaced a predetermined distance from a hitting position, and a control part 30 which controls the hitting member 10, receives a measurement signal of the vibration measurement sensor 20, and determines a level of wall thinning.

As illustrated in the drawing, the hitting member 10, which is a device installed on the pipe T for hitting the pipe T, includes a hammer which is operated by a driving means such as a piston. The driving means may be a motor or a pneumatic piston rather than the hydraulic piston. Further, although not illustrated, a portable hammer may be used rather than the hammer having the driving means. The driving means may include various other devices, as long as the hammer may hit the pipe T with a predetermined impulse.

When the portable hammer is used, like a second embodiment of the present invention which will be described later, it is configured so that natural frequency information may be also extracted from an auto power spectrum APS of a signal measured by the vibration measurement sensor 20 in a natural frequency measuring process.

The control part 30 is connected with the hitting member 10 and the vibration measurement sensor 20 to transmit a control signal or receive a measured signal. When the wall thinning uniformly occurs in the pipe T, a natural frequency is lower than that of a normal pipe T. The control part 30 may estimate the level of the wall thinning of the pipe T by tracing a change in the natural frequency. If a lower natural frequency than the natural frequency measured at the normal pipe is measured, an operator can recognize that wall thinning occurs in the pipe. When a notebook or the like is used as the control part 30, the control part 30 may include a data storage storing natural frequency data generated according to each wall thinning state of the pipe, a signal processing part and so on.

Further, when the wall thinning locally occurs in the pipe T, the measured natural frequency is branched into two or more. At this time, it may be determined whether there is wall thinning in the pipe T and a state thereof by observing the branching phenomenon of the natural frequency.

The natural frequency in a circumferential direction of the pipe may be measured by combining the signal of the hitting member 10 and the signal of the vibration measurement sensor 20, which are measured by the apparatus for detecting the pipe wall thinning. The natural frequency may be expressed by the following Equation 1.

$$f_i = \frac{\lambda_i}{2\pi R} \sqrt{\frac{E}{\rho(1-v^2)}} \quad \text{Equation 1}$$

At this time, $f_i$ is the natural frequency in an i-th degree (i=2, 3, 4, . . . ), R is an inner diameter of the pipe, E is an elastic coefficient, p is a density of the pipe and v is a Poisson's ratio.

At this time, $\lambda_i$ is a coefficient defined by the following Equation 2.

$$\lambda_i = \frac{1}{\sqrt{12}} \frac{t}{R} \frac{i(i^2-1)}{\sqrt{1+i^2}} \quad \text{Equation 2}$$

At this time, t is a thickness of the pipe.

It may be understood from Equation 1 and Equation 2 that the natural frequency of the pipe is changed according to a thickness and a hardness of the pipe. As described above, a pipe having a thinned thickness due to the pipe wall thinning has the lower natural frequency than the normal pipe.

The pipe is deformed into a certain shape, and this is referred to as a mode shape. The natural frequency and the mode shape of the pipe have an infinite number of degrees. However, in practice, a low degree of the natural frequency and the natural mode are main observation objects. The lowest degree is 1, and as a value thereof increases, the degree is designated as 2, 3, 4, . . . , in sequence.

Figure 9A:
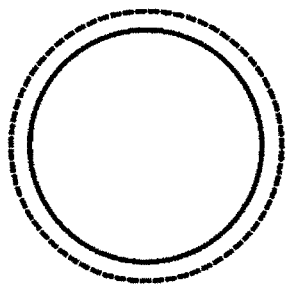
FIG. 9A, FIG. 9B and FIG. 9C are views illustrating a natural mode shape of the pipe.
Figure 9B:
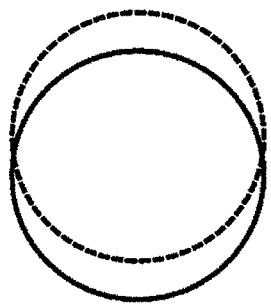
Figure 9C:
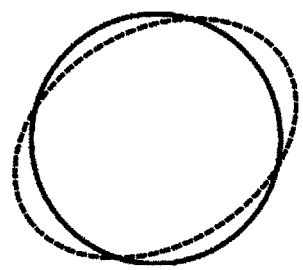

As illustrated in FIG. 9, the second and higher degrees of the mode shape are radially expressed as sin iθ. In a proposed method of the present invention, the natural frequency and the mode shape among the second to fifth degrees are established as the objects to be measured and monitored. That is, in the case of the first degree, the mode shape is radially expressed as sin θ. In the case of the second degree, the mode shape is radially expressed as sin 2θ.

The pipe T having a normal thickness or the pipe of which the thickness is uniformly reduced in the circumferential direction has one natural frequency and natural mode. However, since the pipe of which the thickness is locally reduced by the wall thinning has a different hardness in the circumferential direction, the natural frequency is branched into two or more in the same degree. By observing the branching phenomenon of the natural frequency, whether there is pipe wall thinning and a state thereof may be found. That is, when the pipe wall thinning occurs locally, a position of the wall thinning and a level thereof can be found.

A measuring process of the apparatus for detecting the pipe wall thinning according to the first embodiment of the present invention, as described above, is as follows.

Figure 7:
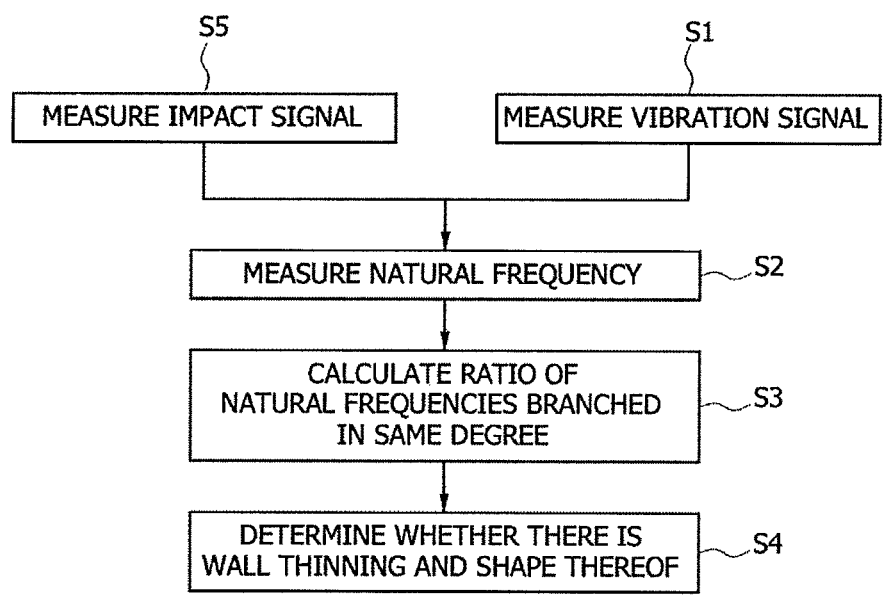
FIG. 7 is a flowchart illustrating a method of detecting local wall thinning in a pipe according to the first embodiment of the present invention.

As illustrated in FIG. 7, a measuring process S1 of installing the hitting member 10 and the vibration measurement sensor 20 at the pipe T to be measured, driving the hitting member 10 to hit the pipe T, and measuring a vibration signal measured by the vibration measurement sensor 20 is performed. At this time, the hitting member 10 has a structure in which a separate driving means is installed at a hammer to automatically hit the pipe. Further, an impact signal measuring process S5 of measuring an impact signal generated when the hitting member 10 hits the pipe is performed with the measuring process S1. The hitting member 10 hits the pipe with a value predetermined by the control part.

After the measuring process S1 and the impact signal measuring process S5, the control part 30 performs a natural frequency measuring process S2 of measuring (calculating) the natural frequency of the pipe T based on the impact signal and the vibration signal of the pipe T.

Then, a calculating process S3 in which the control part 30 calculates a ratio or a difference value between natural frequencies of the pipe T that are branched in the same degree based on the measured natural frequency is performed.

A determining process S4 of comparing the value calculated in the calculating process S3 with the natural frequency branched by each shape of the pipe and stored as data in the control part 30, and estimating whether there is wall thinning and the shape of the wall thinning is performed, and whether there is wall thinning and a shape thereof are estimated.

Also, a measuring process of the apparatus for detecting the pipe wall thinning according to the second embodiment of the present invention is as follows.

Figure 8:
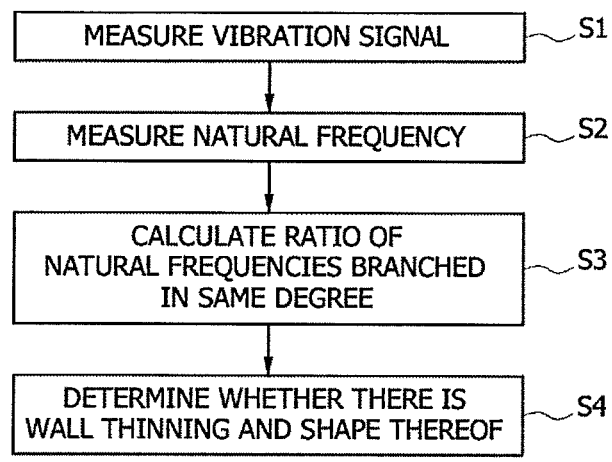
FIG. 8 is a flowchart illustrating a method of detecting the local wall thinning in the pipe according to the second embodiment of the present invention.

As illustrated in FIG. 8, a measuring process S1 of installing the vibration measurement sensor 20 at the pipe T to be measured, hitting the pipe T with the hitting member 10, and measuring a vibration signal measured by the vibration measurement sensor 20 is performed. At this time, the hitting member 10 has a structure in which a user hits the pipe using a portable hammer. As the hitting member 10, any kind of tools which may generate the impact signal from the pipe T may be used.

After the measuring process S1, the control part 30 performs a natural frequency measuring process S2 of measuring the natural frequency of the pipe T based on the vibration signal of the pipe T. At this time, when the portable hammer is used, the natural frequency measuring process S2 is configured to extract the natural frequency information from the APS of the signal measured by the vibration measurement sensor 20. Specifically, when using this method, since the natural frequency of the pipe may be obtained by measuring an arbitrary impact signal using an accelerometer and then observing only the APS thereof, this method includes one accelerometer and a portable spectrum analyzer, and may be applied on the spot using only the two elements. The APS is a signal processing method which has been widely used in the art.

Then, a ratio calculating process S3 in which the control part 30 calculates a ratio of natural frequencies of the pipe T that are branched in the same degree based on the measured natural frequency is performed.

A determining process S4 of comparing the value calculated in the calculating process S3 with the natural frequency branched by each shape of the pipe and stored as data in the control part 30, and estimating whether there is wall thinning and the shape of the wall thinning is performed, and whether there is wall thinning and the shape thereof are estimated.

To check the validity of the measuring method of the present invention, first, the natural frequency of the pipe was analytically found using a finite elements method FEM.

As illustrated in FIGS. 2A-2D, in a pipe having an outer diameter of 115 mm and a thickness of 13.5 mm, the normal pipe T and the wall-thinned pipes T1, T2, T3 and T4 having different thickness reduction amounts were two-dimensionally modeled along each cross-section, and then the natural frequency and natural mode were analyzed.

In the wall-thinned pipes T1, a radius R of an inner groove portion (wall-thinned groove portion) is 10.5 mm, and a distance a between a central axis and a center point of the groove portion is 40 mm. At this time, the thickness reduction amount is 2.3%.

In the wall-thinned pipes T2, a radius R of an inner groove portion (wall-thinned groove portion) is 20.5 mm, and a distance a between the central axis and the center point of the groove portion is 30 mm. At this time, the thickness reduction amount is 3.9%.

In the wall-thinned pipes T3, a radius R of an inner groove portion (wall-thinned groove portion) is 30.5 mm, and a distance a between the central axis and the center point of the groove portion is 20 mm. At this time, the thickness reduction amount is 6.0%.

In the wall-thinned pipes T4, a radius R of an inner groove portion (wall-thinned groove portion) is 40.5 mm, and a distance a between the central axis and the center point of the groove portion is 10 mm. At this time, the thickness reduction amount is 10.0%.

As illustrated in FIGS. 3A-3B, in the analyzed results, it may be confirmed that, as the level of the wall thinning is increased, the natural frequency in all degrees is reduced, and the natural frequency is branched into two in each degree.

Through the finite elements analysis, it may be confirmed that, in a change of the natural frequency when the thickness reduction is the same but the wall-thinning shape is different, a change state in the natural frequency and the branching level of the natural frequency in the same degree are changed according to the shape of the wall thinning.

That is, the analysis was performed with respect to the three pipes T5, T6 and T7, in each of which the thickness reduction amount is maintained to be the same as the wall-thinned pipe T1 of FIGS. 2A-2D having a thickness reduction amount of 2.3%, but the shape of the wall thinning is different. At this time, the wall-thinned pipes T5, T6 and T7 have the shapes illustrated in FIGS. 4A-4C. In the drawing, the wall thinning is formed at a right center portion of each pipe, and the thickness reduction amounts are the same as each other, but the shapes of the wall thinning are different from each other. A result table is shown in FIGS. 5A-5B. As illustrated in FIGS. 5A-5B, it may be confirmed that the change state of the natural frequency and the branching level of the natural frequency in the same degree are changed according to the shapes of the wall thinning.

The ratio between the natural frequencies branched in the same degree is shown in the graphs of FIGS. 5A-5B. It may be confirmed that, as the wall thinning is generated to be deep in a narrow range, the ratio between the natural frequencies is increased.

As described above, the shape of the pipe and the level of the wall thinning are measured variously, and stored in a database created in the control part 30. Then, when the pipe is inspected, the value measured through the apparatus to detect the pipe wall thinning is compared with the database, and thus the level of the wall thinning of the pipe and the shape thereof may be determined.

The validity of the measuring method of the present invention was experimentally verified.

A carbon steel test specimen having the same dimensions as the wall thinned pipe shown in FIGS. 2A-2D was manufactured, and the natural frequency thereof was measured experimentally.

Figure 6B:
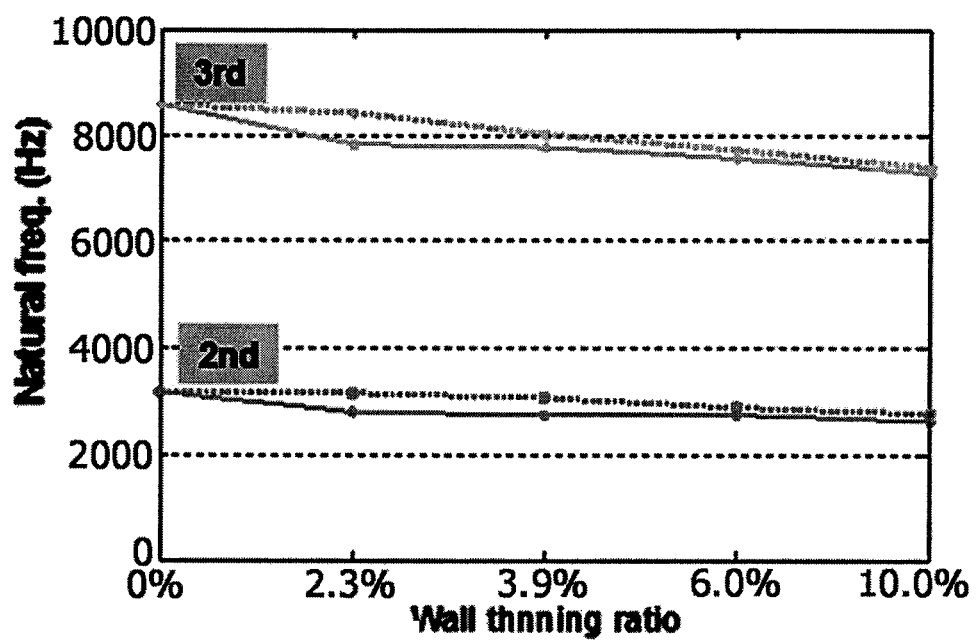

As illustrated in FIGS. 6A-6B, the change in the natural frequency of the pipes according to the level of the wall thinning may be obtained.

As described above, the change in the natural frequency and the branching phenomenon of the natural frequency in the same degree according to the position and the shape of the wall thinning are stored in the database created in the control part, and inspection regarding whether there is wall thinning in the pipe to be measured through the apparatus for detecting the pipe wall thinning may be rapidly performed, and thus the shape of the wall thinning may be estimated.

According to the apparatus for detecting the pipe wall thinning and the method thereof as described above, since whether there is wall thinning and the shape of the wall thinning can be rapidly determined when there are many pipes to be inspected, it is possible to quickly and precisely select the targets of the wall thinning to be monitored, and thus to reduce the inspection time.

Further, according to the apparatus for detecting the pipe wall thinning and the method thereof as described above, the utilization thereof can be enhanced by the simple combination of the hitting member and the vibration measurement sensor which are attached to the pipe, or the simple structure in which one vibration measurement sensor is attached to the pipe and the pipe is hit by the portable hammer.

It will be apparent to those skilled in the art that various modifications can be made to the above-described exemplary embodiments of the present invention without departing from the spirit or scope of the invention. Thus, it is intended that the present invention cover all such modifications provided they come within the scope of the appended claims and their equivalents.

What is claimed is:

1. A method of determining wall thinning in a pipe, comprising:
   measuring a vibration signal from a pipe using a vibration measurement sensor when the pipe is hit;
   measuring a natural frequency of the pipe; and
   calculating a ratio or a difference value between natural frequencies of the pipe, which are branched in the same degree, based on the measured natural frequency; and
   determining whether there is wall thinning and a shape thereof based on the calculated value.

2. The method of claim 1, further comprising:
   hitting the pipe using a hitting member installed on the pipe; and
   measuring vibration of the hitting member before measuring the natural frequency of the pipe.

3. The method of claim 1, further comprising:
   hitting the pipe using a portable hammer,
   wherein measuring the natural frequency of the pipe comprises extracting the natural frequency from an auto power spectrum APS of the measured vibration signal.

4. An apparatus for detecting wall thinning, comprising:
   a vibration measurement sensor which measures a vibration signal generated from a pipe to be measured by being hit with a hitting member to calculate a natural frequency; and
   a control part which compares the natural frequency calculated from the vibration signal measured from the vibration measurement sensor with a natural frequency generated from a normal pipe in which wall thinning does not occur, and determines a level of the wall thinning of the pipe,
   wherein the natural frequency is reduced when the wall thinning occurs uniformly in the pipe, and the control part detects this to determine the level of the wall thinning of the pipe.

5. The apparatus of claim 4, wherein, when the hitting member is a portable hammer, the control part measures an auto power spectrum APS upon measuring of the natural frequency, and extracts the natural frequency.

6. An apparatus for detecting wall thinning, comprising:
   a vibration measurement sensor which measures a vibration signal generated from a pipe to be measured by being hit with a hitting member to calculate a natural frequency; and
   a control part which compares the natural frequency calculated from the vibration signal measured from the vibration measurement sensor with a natural frequency generated from a normal pipe in which wall thinning does not occur, and determines a level of the wall thinning of the pipe,
   wherein, when the wall thinning locally occurs in the pipe, the natural frequency is branched into two or more in the pipe of which a thickness is locally reduced, and the control part observes a branching phenomenon of the natural frequency to determine whether there is wall thinning in the pipe and a state thereof.

* * * * *